US012584092B2

(12) United States Patent
Baumstuemmler et al.

(10) Patent No.: US 12,584,092 B2
(45) Date of Patent: Mar. 24, 2026

(54) USE OF A MICROJET REACTOR FOR PROCESSING BIOMASS

(71) Applicant: Mybiotech GmbH, Ueberherrn (DE)

(72) Inventors: Bernd Baumstuemmler, Saarlouis (DE); Akif Emre Tuereli, Ueberherrn (DE); Felix Penth, Lebach (DE); Daniel Mueller, Ueberherrn (DE); Rudolf Krumbholz, Merchweiler (DE)

(73) Assignee: Mybiotech GmbH, Ueberherrn (DE)

( * ) Notice: Subject to any disclaimer, the term of this patent is extended or adjusted under 35 U.S.C. 154(b) by 1135 days.

(21) Appl. No.: 17/604,224

(22) PCT Filed: May 13, 2020

(86) PCT No.: PCT/DE2020/100408
§ 371 (c)(1),
(2) Date: Oct. 15, 2021

(87) PCT Pub. No.: WO2020/228908
PCT Pub. Date: Nov. 19, 2020

(65) Prior Publication Data
US 2022/0204915 A1 Jun. 30, 2022

(30) Foreign Application Priority Data
May 13, 2019 (DE) ...................... 10 2019 112 382.8

(51) Int. Cl.
*C12M 1/00* (2006.01)
*C12M 1/26* (2006.01)
*C12M 3/06* (2006.01)

(52) U.S. Cl.
CPC ............ *C12M 47/06* (2013.01); *C12M 23/16* (2013.01); *C12M 29/06* (2013.01); *C12M 29/14* (2013.01); *C12M 33/12* (2013.01)

(58) Field of Classification Search
CPC ...... C12M 47/06; C12M 23/16; C12M 29/06; C12M 29/14; C12M 33/12; B01J 3/008; B01J 19/0093
See application file for complete search history.

(56) References Cited

U.S. PATENT DOCUMENTS 6,699,706 B1 * 3/2004 Brooks .................... C12N 1/06
435/298.2
8,697,131 B2 4/2014 Tuereli et al.
(Continued)

FOREIGN PATENT DOCUMENTS

DE 101 41 054 A1 3/2003
DE 10 2009 008 478 A1 8/2010
(Continued)

OTHER PUBLICATIONS

International Search Report in PCT/DE2020/100408, mailed Aug. 3, 2020.

*Primary Examiner* — William H. Beisner
*Assistant Examiner* — Danielle B Henkel
(74) *Attorney, Agent, or Firm* — Collard & Roe, P.C.

(57) ABSTRACT

The invention relates to the use of microjet reactor for processing biomass. The cell lysis of flowable biomass is thereby carried out by means of multiple high-speed liquid jets which collide with one another, wherein the liquid jets contain the cells or consist wholly of the flowable cell mass, wherein intact or wholly or partially lysed biomass is added to at least one of the colliding high-speed liquid jets, and an extraction takes place simultaneously with the collision of the liquid jets or subsequently thereto. The lysis of the cells is initiated or facilitated by the forces that occur on acceleration, introduction of the acceleration, collision of the jets and mixing of the jet constituents.

10 Claims, 4 Drawing Sheets

(56)                    References Cited

U.S. PATENT DOCUMENTS

Figure 1:
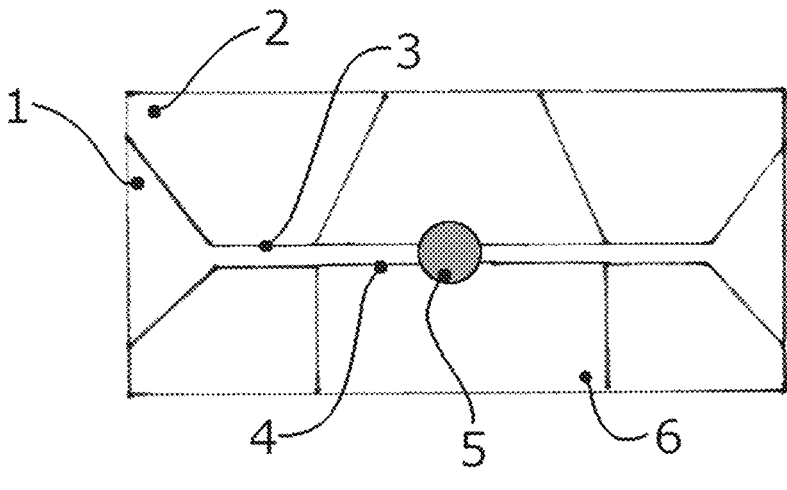

2003/0007416 A1*   1/2003   Shechter ................. B01F 25/23
                                                              366/162.4
2013/0330767 A1*  12/2013   Liddell .................. C12M 47/06
                                                              435/259
2016/0051956 A1    2/2016   Penth et al.
2019/0030497 A1    1/2019   Baumstuemmler et al.

FOREIGN PATENT DOCUMENTS

DE      10 2016 101 232  A1     7/2017
DE      10 2017 110 292  A1    11/2018
DE      10 2017 110 293  A1    11/2018
EP           1 165 224  B1     9/2002
WO            00/61275  A2    10/2000

* cited by examiner

USE OF A MICROJET REACTOR FOR PROCESSING BIOMASS

CROSS REFERENCE TO RELATED APPLICATIONS

This application is the National Stage of PCT/DE2020/100408 filed on May 13, 2020, which claims priority under 35 U.S.C. § 119 of German Application No. 10 2019 112 382.8 filed on May 13, 2019, the disclosure of which is incorporated by reference. The international application under PCT article 21(2) was not published in English.

The invention relates to the use of a microjet reactor for the cell lysis of flowable biomass.

A large number of biological, biotechnological, biopharmaceutical and increasingly also other industrial processes are nowadays dependent on the production of usable valuable substances by a wide variety of very different microorganisms, plant or animal tissues. A prominent example is the production of insulin and insulin analogues from genetically modified microorganisms. However, with advancing climate change and the inherent finiteness of fossil fuels, even fuels that are in principle renewable, for example, are coming into the focus of research and industry, which is aimed for the most part at lipid production from microalgae.

A population with an increasingly more health-conscious lifestyle is continuously increasing the need for food supplements such as the omega-3 fatty acids, including especially EPA (eicosapentaenoic acid) and DHA (docosahexaenoic acid). However, the greatest part of this need is currently being met by the use of fish oil, and there are considerable doubts about the sustainability of fishing for obtaining fish oil. The intake of omega-3 fatty acids from animal sources is also a problem for population groups with a vegetarian or vegan lifestyle. There is therefore a great interest in omega-3 fatty acids from other sources, in particular in obtaining omega-3 fatty acids from the production of microorganisms such as microalgae, cyanobacteria or yeasts.

However, the omega-3 fatty acids are often not present freely in the individual microorganisms, nor are they released into the culture medium. Rather, they are often bound in the form of various lipids such as triglycerides, phospholipids, galacto- or glyco-lipids and are constituents of the cell membrane or other cell organelles. The fatty acids can also be constituents of the cells in the form of lipid vesicles. It is common to all these forms that the extraction of the lipids is made more difficult by the bound form or the inclusion within the cell and in the cell organelles.

Of particular interest is thus cell lysis and thus the destruction or damaging of the cell walls and cell membranes of individual cells or cell structures of various kinds which have been rendered flowable, in order to obtain access to the valuable substances contained in the cell. Destruction means in this context that the cell membrane or cell wall is damaged to such an extent that the cell interior is freed, by opening parts of the cell membrane or cell wall, to such an extent that material exchange with the surroundings can take place unhindered or almost unhindered, or a delimitation of the cell interior with respect to the surroundings can no longer clearly take place. Damaging of the cell wall means in this context that the structure of the cell wall or cell membrane is damaged to such an extent that material exchange between the cell interior and the surroundings can take place through cracks or holes in the cell wall or cell membrane, bypassing the cell's own transport mechanisms.

This definition can likewise also be applied to the cell organelles of the cells, which are likewise protected by cell membranes.

According to current prior art, microbial cell lysis is achieved by various processes. There is known to the person skilled in the art, for example, a process in which small volumes can reliably be lysed by means of immersion of an ultrasonic sonotrode in a batch process. In addition, there are also through-flow processes in which the sonotrode is immersed in a closed chamber through which flow takes place. In addition to poor scalability as a result of a high investment volume, a disadvantage of these processes is the high degree of wear of the sonotrode, wherein the metallic wear debris of the sonotrodes is necessarily found in the product. In this process, in addition to the high noise load, local overheating often occurs, which can be responsible for a reduction in yield in the case of temperature-sensitive samples. In addition there is also the process of so-called "bead milling", in which cell lysis takes place in a lysis vessel by the addition of grinding bodies and agitation of the grinding bodies. Disadvantages of this process are the poor scalability of the process and its availability for only small sample volumes.

There is likewise known the so-called "French press" process, according to which a discrete sample volume is brought to high pressure by means of a plunger and then pressed through a narrow gap in a valve. Lysis of the cells thereby takes place by the high shear forces that occur. A disadvantage of this process is especially the poor scalability.

There is further known the process of high-pressure homogenisation, in which a cell suspension is pressed at high pressure through an annular gap. By means of shear forces and possible cavitation due to rapid decompression in the gap, as well as impact forces on contact with an impact ring surrounding the annular gap, cells can also be destroyed or damaged in the high-pressure homogeniser. A disadvantage of the use of the high-pressure homogeniser is the necessity for minimum pressures in the range of 700-800 bar, which requires the use of expensive high-pressure components and a corresponding investment volume. A further disadvantage of the process is the wear that occurs on the mostly metallic components of the homogeniser, which are subject to high stresses as a result of cavitation and shear.

A microjet reactor is known from patent specification EP 1 165 224 B1.

DE 101 41 054 A1 describes a jet reactor for carrying out physical and chemical conversion processes at a collision point, located in a gas chamber, of liquid jets, the adjustment of the reactor, the protection of the reactor from damage by cavitation by means of tetrahedrally arranged ceramics beads, and the use of the reactor for homogenisation, dispersion and emulsification.

The dissertation "Nanoparticle preparation Using Novel Microjet Reactor Technology for Enhancing Dissolution Rates of Poorly Water Soluble Drugs" by Akif Emre Türeli describes the use of microjet reactor technology for the specific preparation of nanoparticles. In particular, the dissertation describes the preparation of gastro-resistant nanoparticles of the model substance fenofibrate for oral administration using hydroxypropyl methylcellulose phthalate and low molecular weight chitosan as matrix substances.

DE 10 2017 110 293 A1 relates to a method for the surface modification of encapsulated substances. In this method, at least two liquid streams on the one hand of a substance encapsulated with an encapsulating material and on the other hand of a surface modifier are made to collide in a microjet reactor.

US 2016/051956 A1 relates to an apparatus and a method for the production of dispersions and solids by controlled precipitation, co-precipitation and self-organisation processes in a microjet reactor, wherein a jet of solvent containing at least one target molecule and a jet of non-solvent collide with one another.

DE 10 2017 110 292 A1 describes a process and an apparatus for preparing reaction products by controlled precipitation, co-precipitation and/or self-organisation processes in a microjet reactor, wherein a jet of a first starting material emerging from a first nozzle and a jet of a second starting material emerging from a second nozzle collide with one another at defined pressures and flow rates at a collision point in the reactor chamber of the microjet reactor, wherein the microjet reactor has at least one gas inlet for admitting gas to the reaction chamber and a product outlet for discharging the products in a gas stream.

DE 10 2016 101232 A1 describes a process for preparing emulsions. In this process, at least two liquid streams of liquids that are not miscible with one another are pumped through separate openings of defined diameter in order to achieve a flow speed of the liquid streams of more than 10 m/s, wherein the liquid streams collide with one another at a collision point in a chamber.

DE 10 2009 008 478 A1 relates to the preparation of pharmaceutical active ingredient particles of small particle size by a combination of solvent/non-solvent precipitation and in situ lyophilisation.

The object underlying the invention is to optimise the cell lysis of flowable biomass and/or the extraction of constituents therefrom.

This is achieved according to the invention by the use of a microjet reactor in that the nozzle diameters of the microjet reactor are in the range 50 μm-2000 μm and the hydraulic nozzle primary pressures of the microjet reactor are in the range of 5 1000 bar, the jet is formed by two circular diaphragms or nozzles which are situated at opposite locations of a larger space, and the collision angle of the jets is 90° to 180° wherein multiple liquid jets, to which biomass has been added, collide at speeds between 31 m/s and 447 m/s, wherein intact or wholly or partially lysed biomass is added to at least one of the multiple colliding liquid jets, wherein at least one of the jets is enriched wholly or partially with an extracting agent and an extraction takes place simultaneously with the collision of the liquid jets or subsequently thereto.

According to the invention, the cells in the biomass are wholly or partially destroyed by the forces that occur on acceleration, introduction of the acceleration, collision of the jets and mixing of the constituents of the jets.

In this context, biomass generally means pure or diluted or contaminated substances which are liquid, liquefied or flowable or have been rendered flowable, wherein on the one hand these substances can consist of individual cells or cell structures or on the other hand these substances can consist of mechanically or otherwise pre-comminuted or wholly or partially lysed cells or cell structures or can be metabolites released from such cells. In addition, biomass likewise means extracts or concentrates from such substances, for example amino acids, fatty acids, carbohydrates, extremolytes, metabolites of the cells, or other cell contents or constituents thereof or constituents of the cell walls or cell membranes or mixtures of at least two of the above-mentioned substances.

Biomass likewise means complex compounds of and comprising the above-mentioned substances, for example mixtures containing at least one of the following substances: high and low molecular weight compounds, vitamins, pigments, bioemulsifiers and biosurfactants, biopolymers such as proteins and enzymes, peptides, lipids, DNA, RNA, polysaccharides and lignin.

The cells are, for example, microalgae, bacteria, yeasts, or cells of plant, animal or human origin.

The cells are first brought into a flowable form, for example in the form of a cell suspension, or the diluted or undiluted culture medium is used directly for the further process steps. The now flowable biomass is then accelerated and concentrated into multiple liquid jets. The jets are thereby guided such that they collide with one another frontally or at an obtuse angle.

In this simple embodiment of the invention, multiple effects come to bear in order to destroy the cells. As a result of the acceleration of the liquid jet, kinetic energy for cell lysis is provided on a large scale. The collision of the jets following the acceleration, with the conversion of this energy into mechanical work, ensures that compressive and shear forces occur, which also act on the cells. In a preferred embodiment of the invention, the acceleration is produced by a high primary pressure of a nozzle flow, whereby on the other hand shear forces also act on the cells at the nozzle inlet, since a pronounced reduction in cross section of the flow there forces a high speed about a shear edge. These effects cause lysis of the cell by destroying the cell wall.

This use serves to extract constituents of the biomass. This extraction takes place simultaneously with the collision of the liquid jets or subsequently thereto.

Extraction in this context means physical or chemical procedures which are suitable for the enrichment or depletion of a target product or of an impurity in a substance mixture or a solvent or for the separation of a target product or impurity from a substance mixture or a solvent, or a combination thereof. Specific processes of extraction can be, for example, liquid-liquid extraction, solid-liquid extraction, liquid-gas extraction, gas-liquid extraction, extraction with supercritical fluids, crystallisation, distillation, steam distillation, filtration, permeation, pervaporation, electrophoresis, precipitation, flotation, flocculation, sedimentation, centrifugation or chromatography or further processes known to the person skilled in the art. Extraction additionally means processes which by means of a chemical reaction free constituents of the biomass from a bound form or convert them into a different bound form, or convert constituents of the biomass by means of a chemical reaction. Extraction further means processes which combine multiple of the above-mentioned methods in parallel or in succession.

To this end it can be provided that at least one of the jets is enriched wholly or partially with an extracting agent.

A further preferred use consists in that the housing is filled with gas or is flowed through by gas. The collision thus takes place in a gas atmosphere. The gas atmosphere can on the one hand occur by the spatial configuration of the site of collision of the jets, in that the collision is given sufficient space and the jets are able to form freely. On the other hand, the site of collision can also be flowed through by a gas and the collision product thus transported away by the gas stream.

A further variant of the use consists in that the destruction of the cells is initiated or facilitated by the addition of auxiliary substances to flowable biomass.

The auxiliary substances and the flowable biomass may be in separate liquid jets. Furthermore, the auxiliary substance can be an enzyme, a salt, an organic solvent, an acid or a lye. A mixture of at least two of these substances is also conceivable.

In a further possible use, a gas or liquid gas is introduced into at least one liquid jet before the jet is formed. A gas or a liquid gas is thereby added to the liquid jets prior to the acceleration. The purpose of this gas is to dissolve under high pressure in the cells and to expand on leaving the acceleration section as a result of the pressure drop that occurs and to destroy the cells from the inside out or to perforate the cell wall or cell membrane.

In a further use according to the invention, the liquid jets are heated to a temperature above the normal pressure boiling point of the liquid in question, preferably water, prior to the acceleration. Since the cells consist for a large part of water, a portion of the water will evaporate on leaving the acceleration section as a result of the pressure drop that occurs. The steam that forms inside the cells has the purpose of destroying the cells from the inside out or perforating the cell wall or cell membrane.

In a further embodiment of the invention, reaction and extraction steps that are conventionally carried out downstream are integrated into the lysis process. If, for example, one of the processes according to the invention is used for the cell lysis of microalgae in order to obtain omega-3 fatty acids, it is possible inter alia by the addition of an alcohol, a transesterification catalyst and the provision of heat of reaction to release the lipid-bound fatty acids from the head group by means of esterification and to form the corresponding esters. Other forms of esterification of the fatty acid residues of the lipids are also conceivable, in which, for example, the alcohol is added in alcoholate form. The esterification is achieved according to the invention in that the components necessary for the esterification are mixed into the flowable biomass. This can take place according to the invention before the start of the actual lysis process or more effectively preferably as a result of the collision as a high-speed jet with a liquid jet of the cell suspension. The excellent mixing by the jet collision facilitates and accelerates the esterification, so that a higher yield compared to conventional mixing processes can be achieved in a shorter time.

Similarly, an extraction process can take place in that the now esterified fatty acids in the form of a high-speed jet are made to collide with a liquid jet of the lipophilic extracting agent. The excellent mixing by the jet collision can completely replace the conventional columns, often of complex form, for liquid-liquid extraction.

These reaction and extraction processes mentioned by way of example can be carried out both simultaneously with and after the cell lysis, but in many cases even within the same apparatus. It is also possible in a further embodiment of the invention to mix the reactants, after the lysis process, with the lysed flowable biomass in the conventional manner and to achieve complete mixing by the process according to the invention. It is likewise possible to mix the extracting agents, after the reaction process, where necessary, or correspondingly after the lysis process, with the lysed flowable biomass in the conventional manner and to achieve complete mixing by the process according to the invention.

The object is achieved with an apparatus for processing the biomass in that the apparatus is a microjet reactor, and that an impact body, preferably of ceramics, glass or a metal, is able to be brought into the collision point. By the collision of the liquid jets with an impact plate of a solid material or with an impact body of a solid material which has been introduced into the apparatus, the cell lysis of flowable biomass by destruction of the cell walls under the action of the mechanical forces on impact with the impact body is improved.

A further development of the invention consists in that at least one pump is formed by a cylinder filled with liquid, which cylinder is able to be brought to a pressure between 5 and 1000 bar by means of a compressed gas. This permits a higher pressure and accordingly a higher speed of the colliding liquid jets, which advantageously improves the cell splitting.

It is hereby advantageous that the openings in the housing are gaps or annular gaps.

It is common to all the apparatuses according to the invention that the biomass must be accelerated and jets which can be made to collide must be formed. The acceleration can very generally be brought about in that the biomass is placed under pressure and decompressed to a lower pressure by a reduction in cross section, wherein the flow cross sections are geometrically arranged such that the flows that form collide.

In a preferred embodiment of the invention, called RUPEX (rupturing extractor) hereinbelow, the jet is formed by two circular diaphragms or nozzles which are situated at opposite locations of a larger space. The collision angle of the jets is preferably 90°-180°, preferably 135°-180° and particularly preferably 170°-180°. The collision angle is the smaller of the two angles which are formed by the direct connection of the jet inlets into the collision chamber with the collision point. Preferred forms of the RUPEX use nozzle diameters in the range 50 μm-2000 μm, preferably 200 μm-1500 μm, and hydraulic nozzle primary pressures of 5-1000 bar, preferably of 50-800 bar and particularly preferably of 100-350 bar. The jet speeds are 31 m/s-447 m/s, preferably 100 m/s-400 m/s and particularly preferably 140 m/s-254 m/s. This geometric arrangement allows the jets to collide in the middle chamber of the RUPEX. The interior of the chamber is then filled by the injected liquid during the process and transported out of the chamber at correspondingly increasing pressure.

In a further, particularly preferred embodiment of the invention, the middle chamber of the RUPEX is flowed through by gas, which discharges the injected liquid out of the chamber and thus serves to improve the jet formation and the formation of the collision region. In addition, the collision environment can thus be rendered inert. The chamber pressure is here preferably 0-300 bar, more preferably 1-150 bar and yet more preferably 2-100 bar.

In a further form of the apparatus according to the invention, at least one of the jets consists of a supercritical fluid, or a supercritical fluid is a constituent of at least one of the jets.

In a further form of the apparatus according to the invention, the RUPEX apparatus is operated not continuously but intermittently, such that in each case opposing nozzles simultaneously form short-lasting jets.

An exemplary embodiment of the invention first provides the preparation of a suspension of 10 g of dried *Spirulina platensis* and 190 g of water. This is brought to a pressure of 95 bar by means of a hydraulic membrane pump. The liquid stream is divided into two parts and injected into a RUPEX apparatus with a nozzle size of 200 μm. The collision product leaves the RUPEX apparatus as a result of the pressure that builds up in the collision chamber and is fed back into the priming tank of the pump. The lysis process is complete after half an hour.

A further example first provides the preparation of a *Corynebacterium glutamicum* culture by fermentation. One litre of the fermentation liquor diluted with water in the ratio 1:5 is brought to a pressure of 95 bar by means of a hydraulic membrane pump, the liquid stream is divided into two parts and injected into a RUPEX apparatus with a nozzle size of 200 μm. The collision product leaves the RUPEX apparatus as a result of the pressure that builds up in the collision chamber and is fed back into the priming tank of the pump. The lysis process is complete after one hour.

A further example first provides the preparation of a *Saccharomyces cerevisiae* culture by fermentation. By means of a membrane pump, the undiluted culture is brought to a pressure of 95 bar by means of a hydraulic membrane pump, the liquid stream is divided into two parts and injected into a RUPEX apparatus with a nozzle size of 800 μm. The collision product leaves the RUPEX apparatus as a result of the pressure that builds up in the collision chamber and is fed back into the priming tank of the pump. The lysis process is complete after 5 minutes.

A further example first provides the preparation of a *Curcuma longa* suspension by first drying and chopping 20 g of the roots and then suspending them in 36 g of water and 144 g of ethanol. The suspension is introduced into a cylinder and brought to a pressure of 180 bar by means of a nitrogen gas bottle. The suspension is passed under pressure through a pipe to a RUPEX apparatus and injected through nozzles having a diameter of 1500 μm. In addition to lysis of the cells, an extraction is simultaneously carried out in this step. The extract leaves the RUPEX apparatus with the aid of an inert gas which flows through the RUPEX apparatus.

A further example first provides the preparation of a *Nannochloropsis oceanica* culture by culturing in a photo-bioreactor. By means of two plunger pumps, 100 liters of the undiluted, concentrated culture are brought to a pressure of 320 bar and passed in two pipes to two RUPEX apparatuses and injected through two opposite nozzles having a diameter of 1200 μm and made to collide in the interior of the RUPEX apparatuses. The collision product leaves the outlet of the RUPEX apparatus with the aid of an inert gas, which flows through the RUPEX apparatuses, and flows back into the priming tank of the pumps. The lysis process is complete after 10 minutes. The lysed cell suspension is brought to a pressure of 10 bar by means of a centrifugal pump and injected from one side into a further RUPEX apparatus with a nozzle size of 300 μm. n-Hexane as the extracting agent is brought to a pressure of 10 bar by means of a centrifugal pump and injected into the RUPEX apparatus from the other side. After passing through the entire RUPEX apparatus, a floating phase can be removed as the extract.

A further example first provides the preparation of a suspension of 11 g of *Nannochloropsis oceanica,* 1.3 litres of methanol, 0.2 litre of water and 0.035 litre of sulfuric acid. This suspension is brought to a pressure of 95 bar by means of a hydraulic membrane pump, passed through pipes and heated to 60° C. in a heat exchanger, the substance stream is divided and injected from two sides into a RUPEX apparatus with a nozzle size of 200 μm. The collision product leaves the outlet of the RUPEX apparatus into a tank with an excess pressure of 2 bar and is circulated by the pump. In this process, lysis of the cells and esterification of the *Nannochloropsis* lipids to methyl esters are carried out simultaneously. The process is complete after 3 hours. The fatty acid methyl esters are subsequently extracted by injecting the tank contents into the RUPEX apparatus again from one side with a pressure of 10 bar. 0.5 litre of n-hexane is injected from the other side by means of a membrane pump under a pressure of 10 bar. A floating phase can subsequently be removed from the tank as extract.

Exemplary embodiments of the invention will be described in greater detail hereinbelow with reference to drawings.

In the drawings

Figure 2:
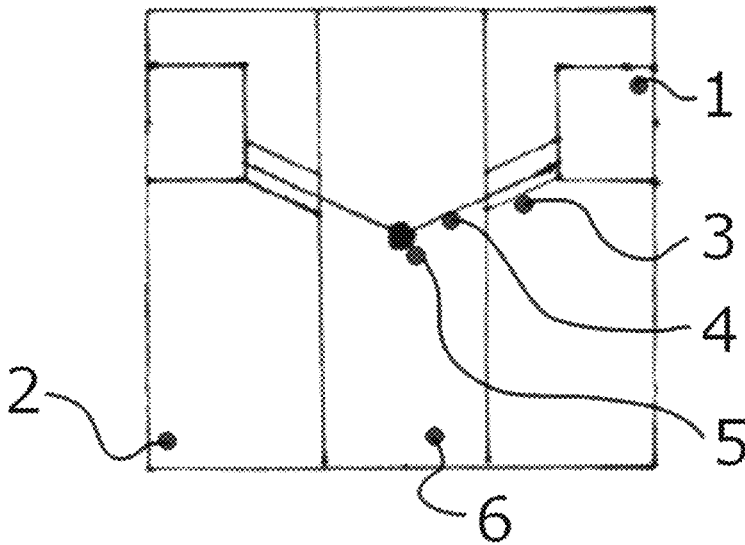
Figure 3:
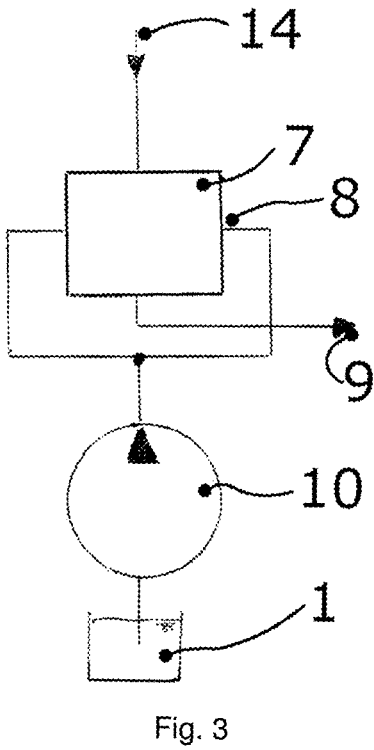
Figure 4:
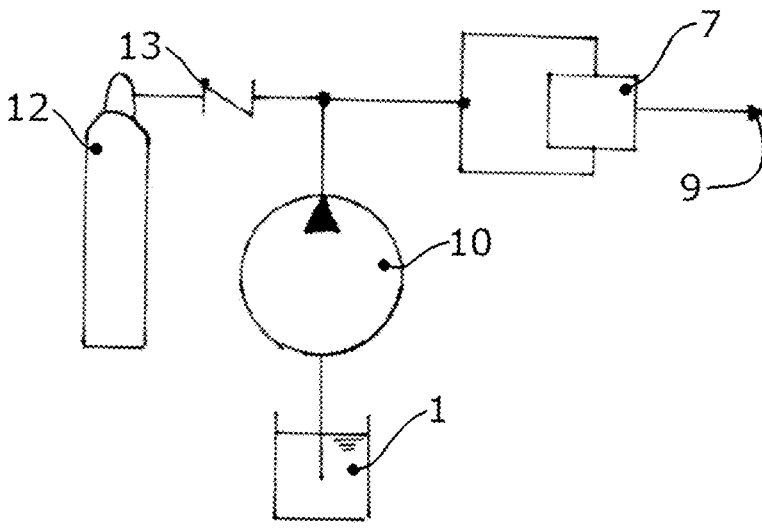
Figure 5:
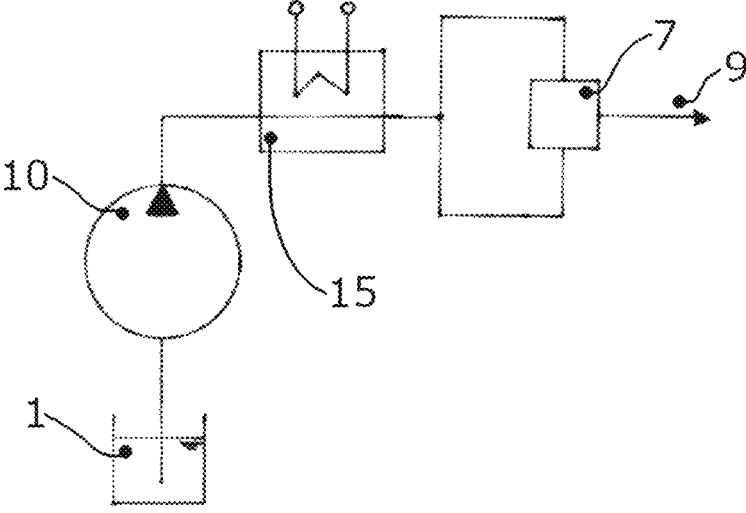
Figure 6:
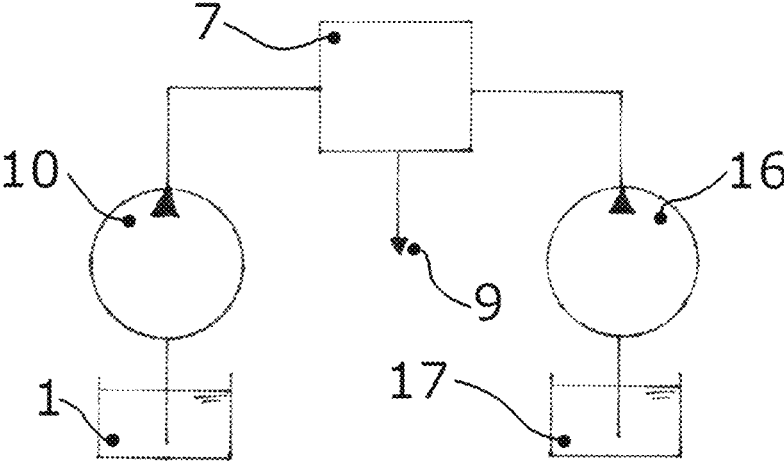
Figure 7:
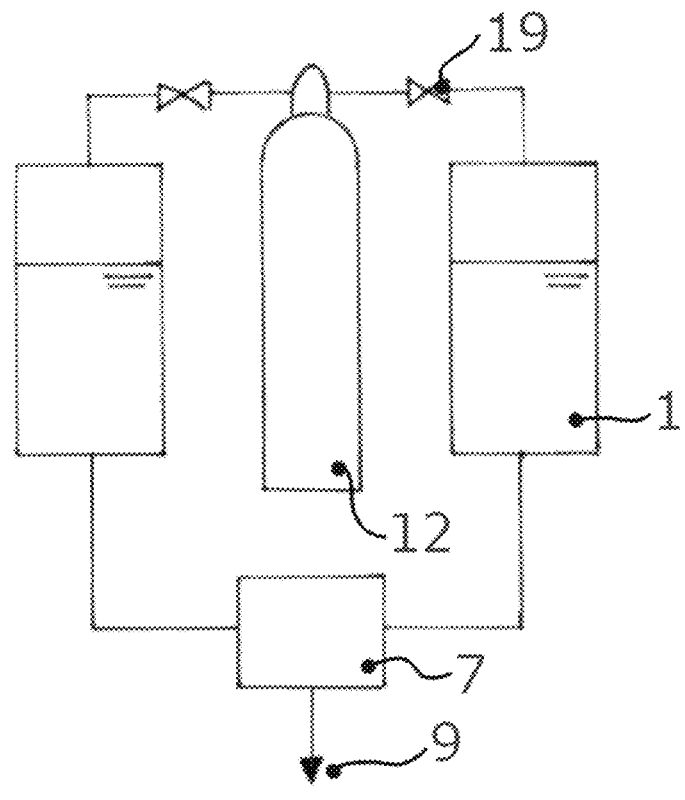
Figure 8:
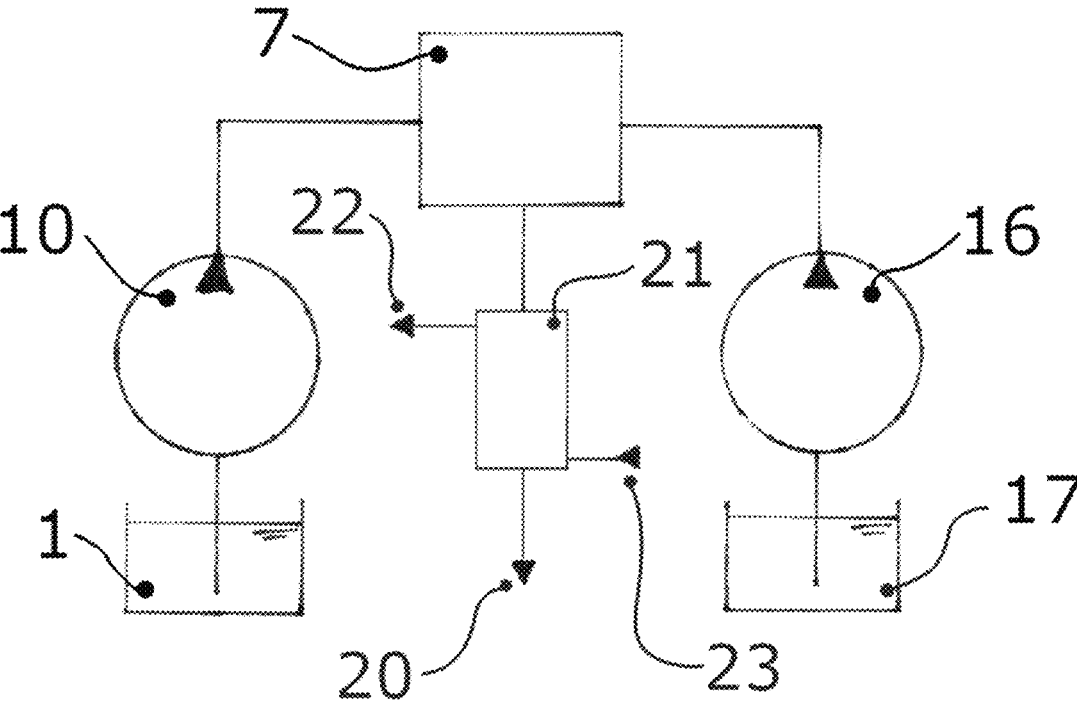

FIG. 1 shows an apparatus according to the invention in cross section,

FIG. 2 shows a further form of the apparatus according to the invention in cross section, FIG. 3 shows a further schematic representation of the apparatus according to the invention, FIG. 4 shows a further schematic representation of the apparatus according to the invention, FIG. 5 shows a further schematic representation of the apparatus according to the invention, FIG. 6 shows a further schematic representation of the apparatus according to the invention, FIG. 7 shows a further schematic representation of the apparatus according to the invention, FIG. 8 shows a further schematic representation of the apparatus according to the invention.

A preferred embodiment of the invention is shown in FIG. 1. The housing of the RUPEX apparatus 2 is thereby depicted, into which the flowable biomass 1 is injected under high pressure from two opposite sides and shaped by a nozzle 3 into jets 4 which collide in the middle chamber (6) of the RUPEX apparatus at the collision point 5. In a further preferred embodiment of the invention, the middle chamber can be filled with gas or flowed through by gas, for example from the top, in order to discharge the substance stream at the bottom.

A further embodiment of the invention is shown in FIG. 2. The housing of the RUPEX apparatus 2 is thereby depicted, into which the flowable biomass 1 is injected under high pressure from two sides and shaped by two nozzles 3, the longitudinal axes of which are at an obtuse angle relative to one another, into jets 4 which collide in the middle chamber 6 of the RUPEX apparatus at an obtuse angle at the collision point 5. In a further preferred embodiment of the invention, the middle chamber can be filled with gas or flowed through by gas, for example from the top, in order to discharge the substance stream at the bottom.

FIG. 3 shows a device-related implementation of the RUPEX apparatus, wherein the flowable biomass 1 is brought to high pressure by means of a pump 10 and injected by means of two nozzles 8 into a chamber 7 in which a collision of the two liquid jets is caused. A gas connection 14 provides for a flow of that gas through the chamber and discharges the collision product through the outlet 9.

A further embodiment of the invention is shown in FIG. 4. A gas or liquid gas 12 is thereby added via a valve 13 to the flowable biomass 1 which has been brought to high pressure by means of a pump 10. The biomass to which gas or liquid gas has been added is injected from two sides into a RUPEX chamber 7, in which a collision of the jets is caused. As it expands, the added gas produces a gas atmosphere in which this collision can take place. The gas discharges the collision product through the outlet 9.

A further embodiment of the invention is shown in FIG. 5. The flowable biomass 1 brought to high pressure by means of a pump 10 is heated by means of a heat exchanger or a heater 15 to a temperature above the normal pressure boiling point of the carrier liquid and injected from two sides into a RUPEX chamber 7 in which a collision of the jets is caused. The decompression of the liquid in the RUPEX chamber to a pressure below its vapour pressure causes at least partial evaporation of the carrier liquid and a discharge of product from the RUPEX chamber through the outlet 9.

A further embodiment of the invention is shown in FIG. 6. The flowable biomass 11 brought to high pressure by means of a pump 10 is injected from one side into a RUPEX chamber 7. From the other side, an aqueous solution of an enzyme 17 brought to high pressure by means of a pump 16 is injected as lysis aid, and the two jets are made to collide in the RUPEX chamber 7. The collision product leaves the RUPEX chamber through the outlet 9.

A further embodiment of the invention is possible with the apparatus from FIG. 6. The flowable biomass 1 brought to high pressure by means of a pump 10 is thereby injected from one side into a RUPEX chamber 7. An extracting agent brought to high pressure by means of a pump 16 is injected from the other side, and the two jets are made to collide in the RUPEX chamber 7. The collision product leaves the RUPEX chamber through the outlet 9.

A further embodiment of the invention is shown by the apparatus in FIG. 7. The flowable biomass 1 is thereby brought to high pressure by means of a precompressed gas or liquid gas 12 and a control valve 19 and injected into the RUPEX chamber 7 from two sides and made to collide. The collision product leaves the RUPEX chamber through the outlet 9.

A further embodiment of the invention is shown by the apparatus in FIG. 8. The flowable biomass 1 brought to high pressure by means of a pump 10 is thereby injected into a RUPEX chamber 7 from one side. An extracting agent 17 brought to high pressure by means of a pump 16 is injected from the other side, and the two jets are made to collide in the RUPEX chamber 7. The collision product is then passed into an extraction chamber 21. The extracting agent containing extract leaves the extraction chamber through the outlet 22. An additional extracting agent or an extraction aid can be fed in via the optional inlet 23. The raffinate leaves the extraction chamber through the outlet 20.

A further embodiment of the invention is possible with the apparatus of FIG. 8. The flowable biomass 1 brought to high pressure by means of a pump 10 is thereby injected into a RUPEX chamber 7 from one side. A biomass 17 brought to high pressure by means of a pump 16 is injected from the other side, and the two jets are made to collide in the RUPEX chamber 7. The pump 10 and the pump 16 and also the biomass 1 and the biomass 17 can be identical. The collision product is then passed into an extraction chamber 21. An extracting agent is fed in via the inlet 23. The extracting agent containing extract leaves the extraction chamber via the outlet 22. The raffinate leaves the extraction chamber through the outlet 20.

The invention claimed is:

1. A method of cell lysing of a flowable biomass, comprising the steps of:

providing a microjet reactor, the microjet reactor having nozzle diameters in a range of 50 μm-2000 μm and hydraulic nozzle primary pressures in a range of 5-1000 bar, forming multiple liquid jets with two circular diaphragms or nozzles which are situated at opposite locations of a larger space, wherein a collision angle of the jets is 90° to 180°, adding wholly or partially lysed biomass to one of the multiple liquid jets and colliding the multiple liquid jets at speeds between 31 m/s and 447 m/s, wholly or partially enriching at least one of the multiple liquid jets with an extracting agent, and performing an extraction simultaneously with or subsequent to a collision of the multiple liquid jets.

2. The method according to claim 1, wherein the nozzle diameters of the microjet reactor are in the range of 200 μm-1500 μm, the hydraulic nozzle primary pressures of the microjet reactor are in the range of 50-800 bar, and the collision angle of the jets is 135° to 180°, wherein the multiple liquid jets, to which biomass has been added, collide at speeds between 100 m/s and 400 m/s.

3. The method according to claim 1, wherein the collision of the multiple liquid jets takes place in a space which is filled with gas or is flowed through by gas.

4. The method according to claim 1, further comprising the step of initiating or facilitating a destruction of the cells by an addition of an auxiliary substance to the flowable biomass, wherein the auxiliary substance comprises at least one of enzymes, salts, organic solvents, acids and lyes.

5. The method according to claim 1, further comprising the step of introducing a gas or a liquid gas into at least one liquid jet of the multiple liquid jets before the at least one liquid jet is formed.

6. The method according to claim 1, further comprising the step of bringing at least one liquid jet of the multiple liquid jets to a temperature above a normal boiling point of the liquid before the at least one liquid jet is formed.

7. The method according to claim 1, wherein at least one of the liquid jets comprises a reactant necessary for further processing.

8. The method according to claim 7, wherein the reactant necessary for further processing comprises a reactant for esterification of lipid-bound or free fatty acids from a biomass comprising a mixture of an acid and an alcohol.

9. The method according to claim 7, wherein the reactant necessary for further processing comprises a reactant for esterification of fatty acids from a biomass comprising a mixture of an alcoholate and the corresponding alcohol.

10. The method according to claim 7, wherein the reactant necessary for further processing comprises a reactant for hydrolysis of lipid-bound or free fatty acids from a biomass comprising a lye.

* * * * *